(12) United States Patent
Trautwein et al.

(10) Patent No.: US 7,922,750 B2
(45) Date of Patent: Apr. 12, 2011

(54) INTERLAMINAR-INTERSPINOUS VERTEBRAL STABILIZATION SYSTEM

(75) Inventors: Frank T. Trautwein, Filderstadt (DE); Ralf Riesinger, Wurmlingen (DE); Gary L. Lowery, Jacksonville, FL (US); Marc R. Viscogliosi, New York, NY (US)

(73) Assignee: Paradigm Spine, LLC, New York, NY (US)

(*) Notice: Subject to any disclaimer, the term of this patent is extended or adjusted under 35 U.S.C. 154(b) by 417 days.

(21) Appl. No.: 11/947,188

(22) Filed: Nov. 29, 2007

(65) Prior Publication Data

US 2008/0228225 A1    Sep. 18, 2008

Related U.S. Application Data

(60) Provisional application No. 60/868,080, filed on Nov. 30, 2006.

(51) Int. Cl.
*A61B 17/88* (2006.01)
(52) U.S. Cl. .................................. 606/279; 606/86 A
(58) Field of Classification Search .......... 606/246–249, 606/99, 86 A, 105; 623/17.11–17.16
See application file for complete search history.

(56) References Cited

U.S. PATENT DOCUMENTS

| | | | |
|---|---|---|---|
| 3,648,691 A | 3/1972 | Lumb et al. | |
| 4,554,914 A | 11/1985 | Kapp et al. | |
| 4,570,618 A | 2/1986 | Wu | |
| 4,573,454 A | 3/1986 | Hoffman | |
| 4,604,995 A | 8/1986 | Stephens et al. | |
| 4,686,970 A | 8/1987 | Dove et al. | |
| 4,773,402 A | 9/1988 | Asher et al. | |
| 4,790,297 A | 12/1988 | Luque | |
| 4,887,595 A | 12/1989 | Heinig et al. | |
| 5,011,484 A | 4/1991 | Breard | |
| 5,366,455 A | 11/1994 | Dove et al. | |
| 5,375,823 A | 12/1994 | Navas | |
| 5,415,661 A | 5/1995 | Holmes | |
| 5,496,318 A | 3/1996 | Howland et al. | |
| 5,540,688 A | 7/1996 | Navas | |
| 5,609,634 A | 3/1997 | Voydeville | |
| 5,645,599 A | 7/1997 | Samani | |

(Continued)

FOREIGN PATENT DOCUMENTS

DE         42 19 939 C2     12/1993

(Continued)

OTHER PUBLICATIONS

International Search Report for International Application No. PCT/US2007/085916 mailed Apr. 28, 2008.

(Continued)

*Primary Examiner* — Eduardo C Robert
*Assistant Examiner* — Christina Negrelli
(74) *Attorney, Agent, or Firm* — Monument IP Law Group

(57) ABSTRACT

An implantable interlaminar-interspinous stabilization system is provided. The system may comprise a U-shaped implantable device having an inferior section, a superior section, a midsection extending therebetween, and pair of lateral walls for engaging a spinous process of a vertebra, each of the lateral walls including an aperture with a countersink for receiving a bone fastener. The system may also include a bone fastener comprising a threaded bolt and a threaded nut for securing the implantable device to the spinous processes. Insertion tools may be provided for aligning the threaded bolt and nut through the apertures of the implantable device.

32 Claims, 10 Drawing Sheets

U.S. PATENT DOCUMENTS

| | | |
|---|---|---|
| 5,672,175 A | 9/1997 | Martin |
| 5,725,582 A | 3/1998 | Bevan et al. |
| 5,733,284 A | 3/1998 | Martin |
| 5,810,815 A | 9/1998 | Morales |
| 5,836,948 A | 11/1998 | Zucherman et al. |
| 5,860,977 A | 1/1999 | Zucherman et al. |
| 5,868,745 A | 2/1999 | Alleyne |
| 5,876,404 A | 3/1999 | Zucherman et al. |
| 5,951,553 A | 9/1999 | Betz et al. |
| 5,961,516 A | 10/1999 | Graf |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,267,764 B1 | 7/2001 | Elberg |
| 6,273,914 B1 | 8/2001 | Papas |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,364,883 B1 | 4/2002 | Santilli |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,436,099 B1 | 8/2002 | Drewry et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,626,944 B1 | 9/2003 | Taylor |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,761,720 B1 | 7/2004 | Senegas |
| 6,796,983 B1 | 9/2004 | Zucherman et al. |
| 6,852,128 B2 | 2/2005 | Lange |
| 6,875,212 B2 | 4/2005 | Shaolian et al. |
| 6,899,713 B2 | 5/2005 | Shaolian et al. |
| 6,902,566 B2 | 6/2005 | Zucherman et al. |
| 2002/0099377 A1 | 7/2002 | Zucherman et al. |
| 2003/0135277 A1 | 7/2003 | Bryan et al. |
| 2003/0153915 A1 | 8/2003 | Nekozuka et al. |
| 2003/0171749 A1 | 9/2003 | Le Couedic et al. |
| 2003/0191470 A1 | 10/2003 | Ritland |
| 2003/0216736 A1 | 11/2003 | Robinson et al. |
| 2004/0019263 A1 | 1/2004 | Jutras et al. |
| 2004/0073215 A1 | 4/2004 | Carli |
| 2004/0106995 A1* | 6/2004 | Le Couedic et al. ....... 623/17.11 |
| 2004/0143332 A1 | 7/2004 | Krueger et al. |
| 2004/0153071 A1 | 8/2004 | Zucherman et al. |
| 2004/0153072 A1 | 8/2004 | Bonutti |
| 2004/0162617 A1 | 8/2004 | Zucherman et al. |
| 2004/0181282 A1 | 9/2004 | Zucherman et al. |
| 2004/0199255 A1 | 10/2004 | Mathieu et al. |
| 2004/0220568 A1 | 11/2004 | Zucherman et al. |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0015095 A1 | 1/2005 | Keller |
| 2005/0055031 A1 | 3/2005 | Lim |
| 2005/0056979 A1 | 3/2005 | Studer et al. |
| 2005/0065514 A1 | 3/2005 | Studer |
| 2005/0075634 A1 | 4/2005 | Zucherman et al. |
| 2005/0101955 A1 | 5/2005 | Zucherman et al. |
| 2005/0113927 A1 | 5/2005 | Malek |
| 2005/0143738 A1 | 6/2005 | Zucherman et al. |
| 2005/0165398 A1 | 7/2005 | Reiley et al. |
| 2005/0196420 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216017 A1 | 9/2005 | Fielding et al. |
| 2005/0228383 A1 | 10/2005 | Zucherman et al. |
| 2005/0228384 A1 | 10/2005 | Zucherman et al. |
| 2006/0030860 A1 | 2/2006 | Peterman |

FOREIGN PATENT DOCUMENTS

| | | |
|---|---|---|
| EP | 0 322 334 A1 | 6/1989 |
| EP | 0 649 636 A2 | 4/1995 |
| EP | 0 806 212 A1 | 11/1997 |
| EP | 1 138 268 A1 | 10/2001 |
| EP | 1 330 987 A1 | 7/2003 |
| EP | 1 442 714 A1 | 8/2004 |
| FR | 2 703 239 | 10/1994 |
| FR | 2 717 675 | 9/1995 |
| FR | 2 722 980 A1 | 2/1996 |
| WO | WO 94/26192 A1 | 11/1994 |
| WO | WO 99/40866 A1 | 8/1999 |
| WO | WO 01/45576 A1 | 6/2001 |
| WO | WO 01/56489 A1 | 8/2001 |
| WO | WO 02/102259 A2 | 12/2002 |
| WO | WO 03/007829 A1 | 1/2003 |
| WO | WO 2004/024010 A1 | 3/2004 |
| WO | WO 2004/073533 A1 | 9/2004 |
| WO | WO 2004/084743 A1 | 10/2004 |
| WO | WO 2005/009300 A1 | 2/2005 |
| WO | WO 2005/020860 A2 | 3/2005 |
| WO | WO 2005/110258 A1 | 11/2005 |
| WO | WO 2006/110578 A2 | 10/2006 |
| WO | WO 2007/000654 A2 | 1/2007 |

OTHER PUBLICATIONS

Written Opinion of the International Searching Authority for International Application No. PCT/US2007/085916 mailed Apr. 28, 2008.

* cited by examiner

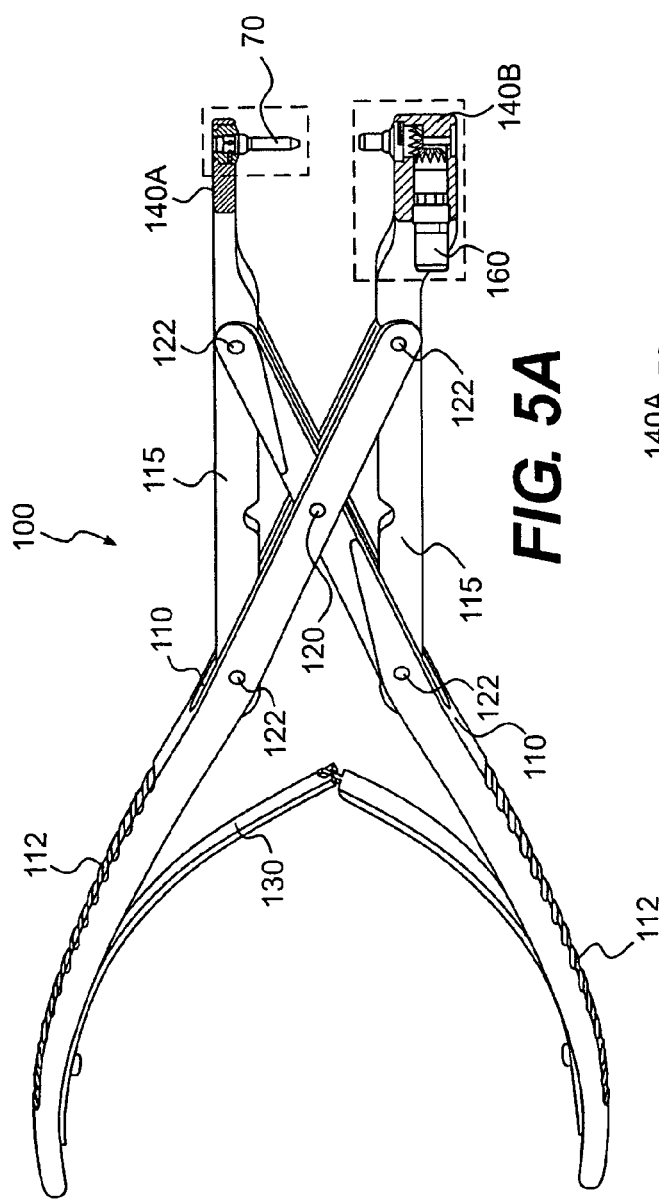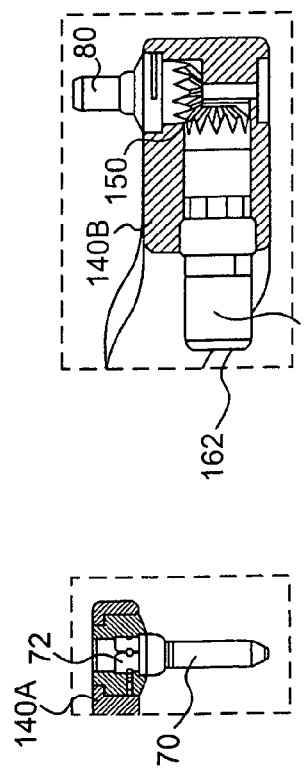

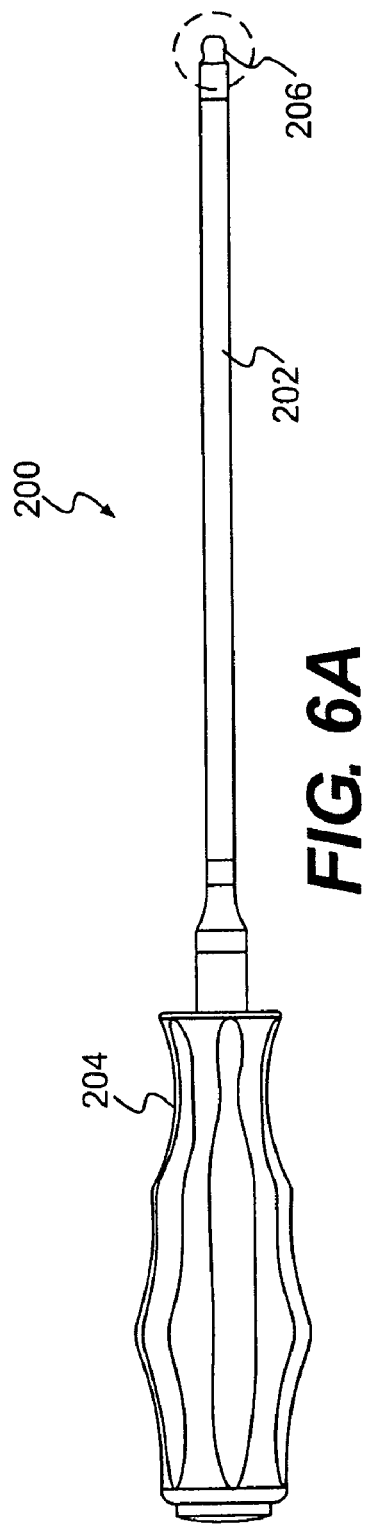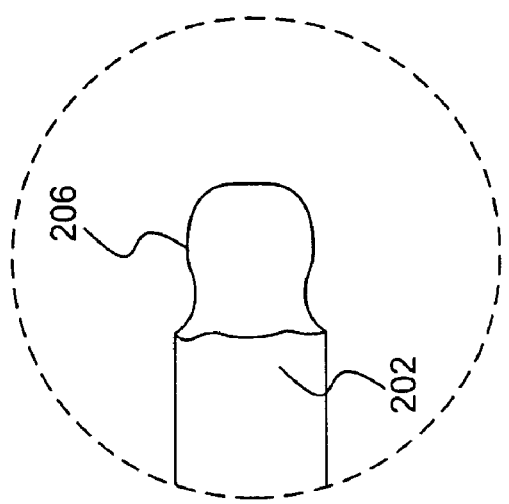
FIG. 6A
FIG. 6B

INTERLAMINAR-INTERSPINOUS VERTEBRAL STABILIZATION SYSTEM

This application claims priority to U.S. Provisional Application No. 60/868,080, filed on Nov. 30, 2006, the contents of which are hereby incorporated in its entirety.

FIELD

The present disclosure relates to devices and methods for treating spinal conditions, including interlaminar-interspinous vertebral stabilization devices and methods of using such devices for stabilizing adjacent vertebrae.

BACKGROUND

Diseases of the spine cause significant morbidity. These diseases include abnormalities of the vertebrae, the intervertebral discs, the facet joints, and connective tissue around the spine. These abnormalities can be due to a number of causes, including mechanical injury or degenerative disc disease. Such abnormalities can cause instability to the spine, allowing the vertebral column to become misaligned and producing micromotion between adjacent vertebrae. Vertebral misalignment and micromotion may result in wear to the vertebral bony surfaces and ultimately cause severe pain. Further, these conditions are often chronic and progressive problems.

The treatments for spinal disorders can include long-term medical management or surgery. Medical management is generally directed at controlling the symptoms, such as pain, rather than correcting the underlying problem. For some patients, this may require chronic use of pain medications, which may alter patient mental state or cause other negative side effects.

Recently, a variety of interspinous stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Currently available interspinous stabilization systems can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. However, it may be desirable to provide a more rigid and secure attachment to the spinous processes. For example, a rigid attachment may be desirable to prevent the interspinous device from migrating or slipping out of position. In addition, a rigid attachment may be desirable to limit movement and promote fusion at a selected vertebral level. Even further, it may be desirable to provide a device that can also fit interlaminarly between adjacent vertebrae, thereby enhancing the stability of the region.

The present disclosure describes an interlaminar-interspinous vertebral stabilization system that can be easily implanted and can be securely attached to the spinous processes while being seated interlaminarly.

SUMMARY

The present disclosure describes an interlaminar-interspinous vertebral stabilization system and a method of using this system for treating spinal instability conditions. The system includes an interlaminar-interspinous vertebral stabilization device adapted for placement between the spinous processes of adjacent vertebrae and a bone fastener for securing the device to the spinous processes. Also provided are insertion tools and methods for using such a system.

One aspect of the disclosure includes an implantable interlaminar-interspinous stabilization system. The system may comprise a U-shaped implantable device having an inferior section, a superior section, a midsection extending therebetween, and pair of lateral walls for engaging a spinous process of a vertebra, each of the lateral walls including an aperture with a countersink for receiving a bone fastener. The system may also include a bone fastener comprising a threaded screw and nut for securing the implantable device to the spinous process. Further, insertion tools may be provided for properly aligning the threaded screw and nut during assembly of the bone fastener through the apertures of the implantable device.

A second aspect of the present disclosure includes an implantable interlaminar-interspinous stabilization system. The system can comprise an implantable device having an inferior section, a superior section, and pair of lateral walls extending from at least one of the inferior section and superior section for engaging a spinous process of a vertebra. A U-shaped midsection extending between the inferior and superior sections enables the device to be positioned interlaminarly between two adjacent vertebrae. Each of the lateral walls can include an aperture for receiving a bone fastener. The system can further include a bone fastener comprising a threaded bolt and a threaded nut for securing the implantable device to the spinous process and an insertion tool for aligning the threaded bolt and nut through the apertures of the implantable device.

A third aspect of the present disclosure includes a method of stabilization of a spine. The method can include selecting a vertebral level to be treated and positioning a U-shaped implant between two spinous processes of the selected vertebral level. The implant may comprise an inferior section, a superior section, a midsection extending therebetween configured to be seated interlaminarly, and a first pair of lateral walls extending from at least one of the inferior section and superior section. The lateral walls are positioned on opposite sides of one of the spinous processes of the selected vertebral level. Further, each of the lateral walls can include an aperture for receiving a bone fastener, and the implant can be secured to at least one of the spinous processes by passing a threaded bolt through the aperture of one of the lateral walls and passing a nut through the aperture of the lateral wall located on the opposite side of the spinous process such that the nut and bolt pass through the spinous process and are joined at a threaded connection.

It is to be understood that both the foregoing general description and the following detailed description are exemplary and explanatory only, and are not restrictive of the disclosure, as claimed.

The accompanying drawings, which are incorporated in and constitute a part of this specification, illustrate several embodiments of the disclosure and together with the description, serve to explain the principles of the disclosure.

Additional objects and advantages of the disclosure will be set forth in part in the description which follows or may be learned by practice of the disclosure. The objects and advantages of the disclosure will be realized and attained by means of the elements and combinations particularly pointed out in the appended claims.

BRIEF DESCRIPTION OF THE DRAWINGS

FIG. 5A illustrates a side view of the insertion tool of FIGS. 4A and 4B with the bone fastener of FIG. 3.

FIG. 5B illustrates an enlarged view of a portion of the insertion tool and a portion of the bone fastener of FIG. 5A.

FIG. 5C illustrates another enlarged view of another portion of the insertion tool and another portion of the bone fastener of FIG. 5A.

FIG. 6A illustrates a side view of a tightening instrument that may be used with the interlaminar-interspinous vertebral stabilization system of FIG. 1.

FIG. 6B illustrates an enlarged view of an end of the tightening instrument of FIG. 6A.

DESCRIPTION OF THE EMBODIMENTS

Figure 1:
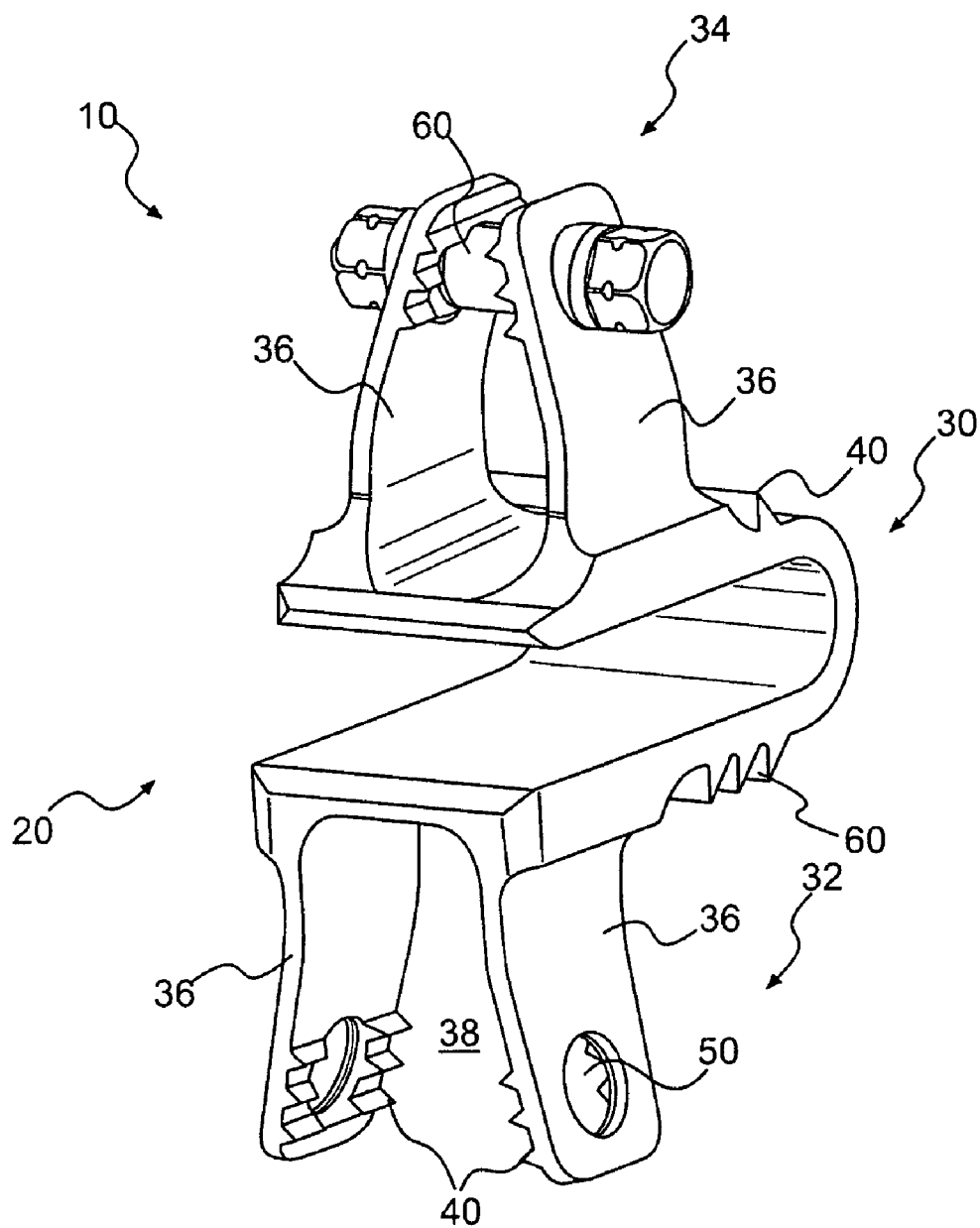
FIG. 1 illustrates a perspective view of an exemplary embodiment of an interlaminar-interspinous vertebral stabilization system.

FIG. 1 shows an implantable interlaminar-interspinous vertebral stabilization system 10 for stabilizing adjacent vertebrae. The system 10 comprises an implantable device 20 configured for placement between the spinous processes of adjacent vertebrae. The device can include one or more bone anchors for securing the device to spinous processes. Further, in one embodiment, the bone anchors can rigidly fix the device with respect to the spinous processes, thereby limiting movement at a selected vertebral level and promoting fusion at that level.

The device 20 may include a spacer body. The spacer body 20 may have various shapes and thicknesses, and can be produced from a variety of different materials. In one embodiment, the spacer body 20 may include a midsection 30 extending between an inferior section 32 and a superior section 34, as shown in FIG. 1. When implanted in a patient, the superior section 34 is configured to contact a portion of a first spinous process, while the inferior section 32 is configured to contact a portion of a second, adjacent spinous process. In one embodiment, the midsection 30, inferior section 32, and superior section 34 may together form a substantially U-shaped spacer body 20, as shown. The spacer body 20 may be configured to be flexible and/or bendable, such as, for example, by providing an extendable and/or compressible midsection 30. The midsection 30 can act as a flexible hinge, allowing the superior section 34 and inferior section 32 to move away from or towards one another. Furthermore, the U-shaped spacer body enables the device 10 to be positioned, or fitted, interlaminarly after implantation, thereby enhancing the stabilization of the adjacent vertebrae.

To engage the spinous processes of adjacent vertebrae, the spacer body 20 may be provided with a pair of lateral walls or brackets 36 that extend from the inferior and superior sections 32, 34, as shown in FIG. 1. Each of the pair of lateral walls 36 defines a stirrup 38 for receiving a spinous process. The spacer body 20 can be provided with lateral walls 36 of various sizes or heights to accommodate variations in patient anatomy. Likewise, the lateral walls 36 of different spacer bodies 20 may be provided at differing locations along the length of the inferior section 32 or superior section 34. The surgeon can thus select a suitably shaped and sized spacer body 20 depending on the particular vertebral level to be supported and the anatomy of the patient.

Further, the lateral walls 36 may also be adjustable with respect to the spacer body 20. For example, in one embodiment, the lateral walls 36 may be formed of a malleable material such that, after implantation, the surgeon may compress the lateral walls 36 together to reduce the gap between the lateral walls 36, thereby securely fixing the spacer body 20 to a spinous process located therein. In addition, the lateral walls 36 may be spread apart to facilitate insertion, as illustrated with the inferiorly located lateral wall 36 of FIG. 1. The lateral walls 36 may be compressed or spread apart, for example, using surgical pliers or forceps.

A number of biocompatible materials are suitable for forming the spacer body 20 of the present disclosure. For example, in one embodiment, the spacer body 20 may be formed from a medical grade metal such as titanium or a titanium alloy. The spacer body 20 may also be formed from a variety of other materials, such as stainless steel, cobalt chrome, ceramics, and/or polymeric materials, such as ultra-high molecular-weight polyethylene (UHMWPE) and polyetheretherketone (PEEK), either alone or in combination with other suitable materials.

To further enhance the ability of the device 10 to be secured to the surrounding bone and soft tissue, the device 10 may include a number of surface modifications. For example, the spacer body 20 may include surface alterations that may facilitate tissue attachment, bonding, or fixation. These surface alterations may include teeth, barbs, beads, surface roughening, or the addition of bioactive agents to one or more sections of the device 10. For example, the device 10 may include one or more barbs 40 for securing the device 10 to bone and/or soft tissue. As shown, the barbs 40 may be located on the spacer body 20, such as on an outer surface of the inferior section 32 and/or superior section 34. Alternatively, or in addition, the barbs 40 may be located on an inner surface of the lateral walls 36. The barbs 40 may help the spacer body 20 securely engage connective tissue or a bony surface of a vertebra, such as the spinous process of the vertebra.

Further, the device 10 may also include roughened or porous surfaces. The roughened or porous surfaces may enhance attachment between implant surfaces and bone. In addition, some porous surfaces may facilitate tissue ingrowth to form a biological bond between sections of the device 10 and the surrounding bone and/or soft tissue. Roughened or porous surfaces may be included on any portion of the device 10.

The surface of the device 10 may also include biologically active agents. These agents may include osteogenic factors to further facilitate bonding between components of the device 10 and the surrounding bone and/or soft tissue. Further, the device 10 may include therapeutic agents such as antibiotics, steroids, anti-thrombotic agents, anti-inflammatory drugs, and/or analgesic agents. In one embodiment, the biologically active agent may be contained in a coating on the device. Alternatively, or in addition, the device may be porous, and the biologically active agent may be contained in the pores of the device. The biologically active agent may be, for example, bone morphogenic protein (BMP) for modulating cartilage or bone growth.

The lateral walls or brackets 36 of the present invention can also include an aperture 50 for receiving a bone fastener to fix the brackets 36 to the spinous process. Such fastening members can ensure that the brackets 36 are pressed flat and/or securely against the spinous process in order to avoid any play of the brackets 36 with respect to the process. Further, the system 10 may act as a fusion-promoting device when the implantable device 20 is fastened to the spinous process in this manner.

Figure 2:
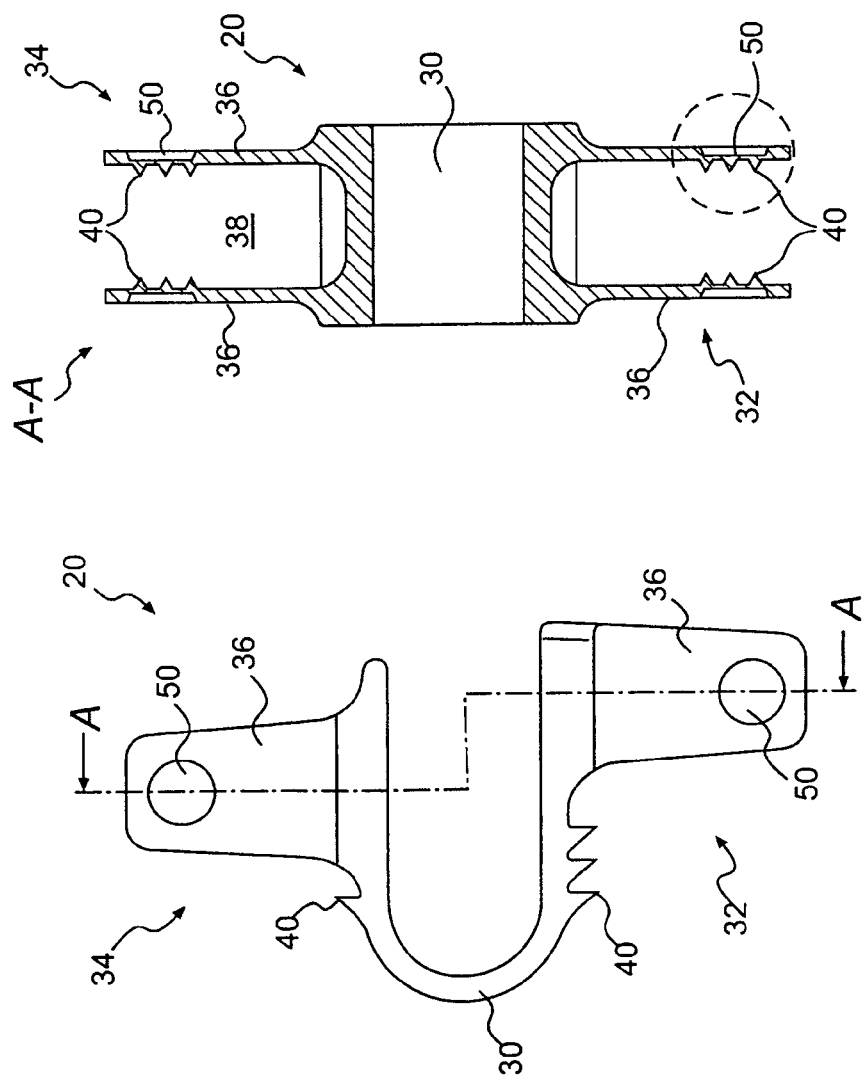
FIG. 2A illustrates a side view of an implantable device of the system shown in FIG. 1.
FIG. 2B illustrates a cut-away back end view of the device of FIG. 2A along line A-A.
FIG. 2C illustrates an enlarged view showing details of FIG. 2B.

The aperture can include a range of sizes and shapes. For example, the aperture 50 may include a countersink 52, as shown in FIG. 2C, to allow for better seating of a bone fastener 60 against the lateral walls 36. Further, as shown in FIG. 2A, the apertures 50 of the inferior and superior sections 32, 34 may be staggered along a longitudinal axis, as the superior section 34 may be shorter in length than the inferior section 32. This feature allows a plurality of the implantable devices 20 to be stacked, or implanted, along the spinal column.

Figure 3:
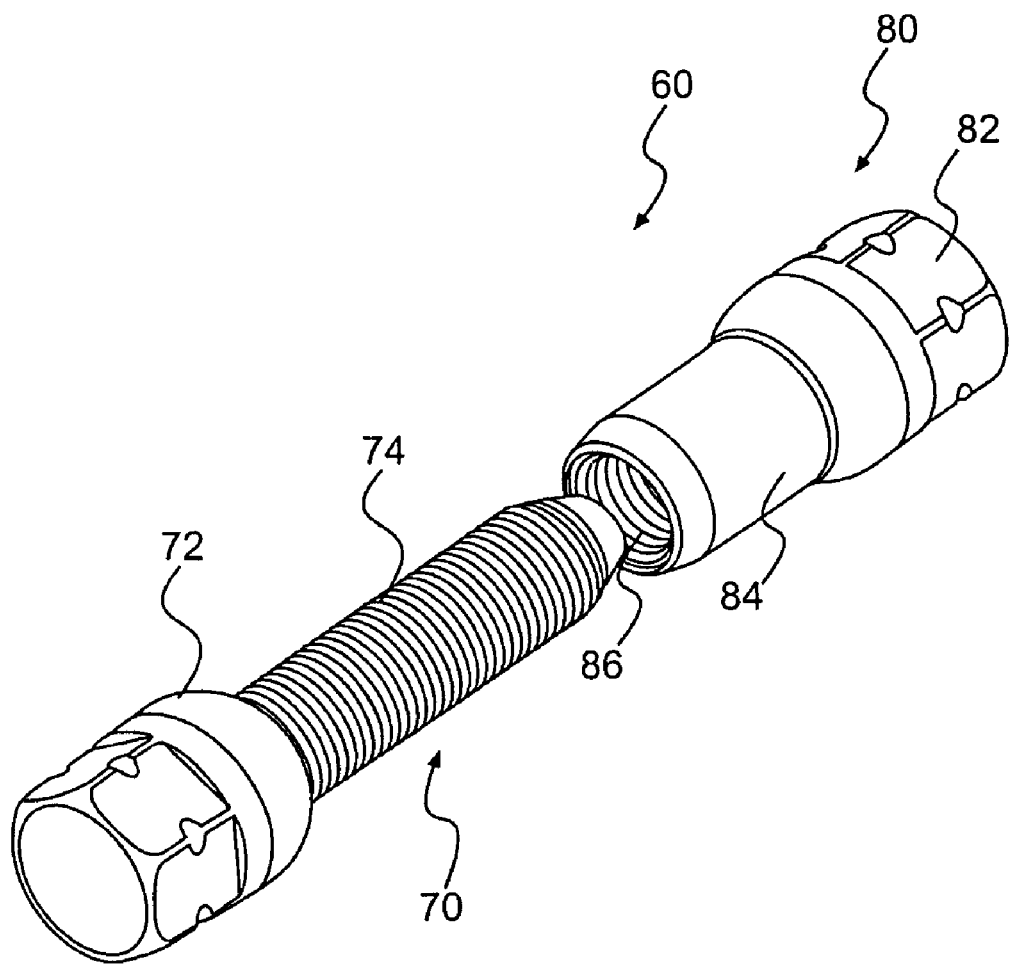
FIG. 3 illustrates a perspective view of a bone fastener of the interlaminar-interspinous vertebral stabilization system, shown in FIG. 1.
Figure 10:
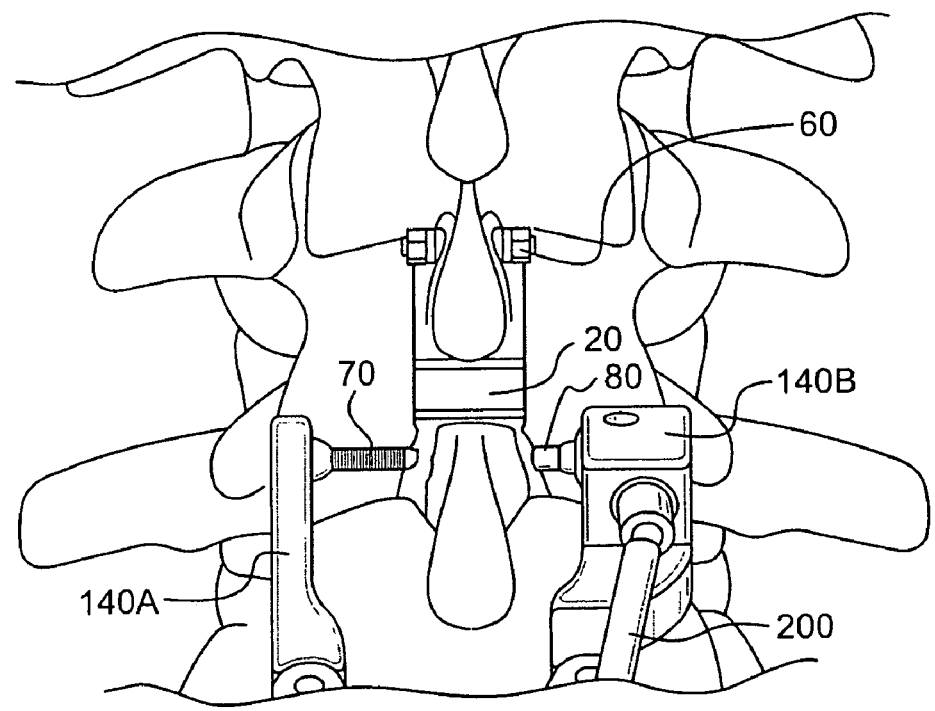
FIG. 10 is a perspective view of a partially-assembled interspinous system, according to one exemplary embodiment.

Turning now to FIG. 3, the bone fastener 60 can include a bolt 70 comprising a head 72 and a threaded, elongate body 74. To secure the bolt 70 within an aperture 50, a nut 80 is provided having a head 82, body portion 84, and threaded inner cavity 86 for receiving the threaded, elongate body 74 of the bolt 70. As the nut 80 is threaded onto the bolt 70, the lateral walls 36 may be drawn together, as shown in FIG. 1. Thus, the bone fastener 60 and spacer body 20 may form a tight, secure connection with the spinous process. In some embodiments, the tight, secure connection between the body 20 and adjacent spinous processes will limit movement at the selected vertebral level, thereby promoting fusion at that level. In other embodiments, the nut 80 and bolt 70 may be tightened sufficiently to prevent the spacer body 20 from moving out of position between the spinous processes, but may be left sufficiently loose so as to allow a small amount of play between the spacer body 20 and spinous processes, so as not to promote fusion, or cause fusion to occur more slowly. Further, in some embodiments, the system 10 can include two bone fasteners 60, so that both the inferior and superior lateral walls 36 can be securely fastened to spinous processes, as shown in FIG. 10 below. Thus, it is contemplated that the device 20, when positioned between the spinous processes of two adjacent vertebrae, may be secured to one spinous process and not the other spinous process, or to both adjacent spinous processes.

Figure 4A:
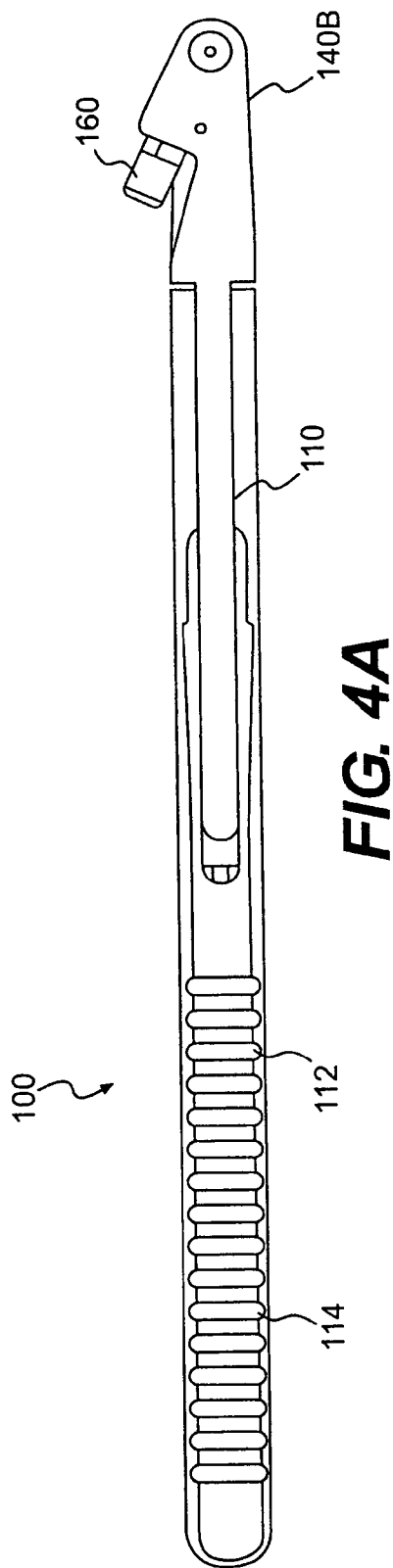
FIG. 4A illustrates a side view of an insertion tool that may be used with the interlaminar-interspinous vertebral stabilization system, according to one exemplary embodiment.
Figure 4B:
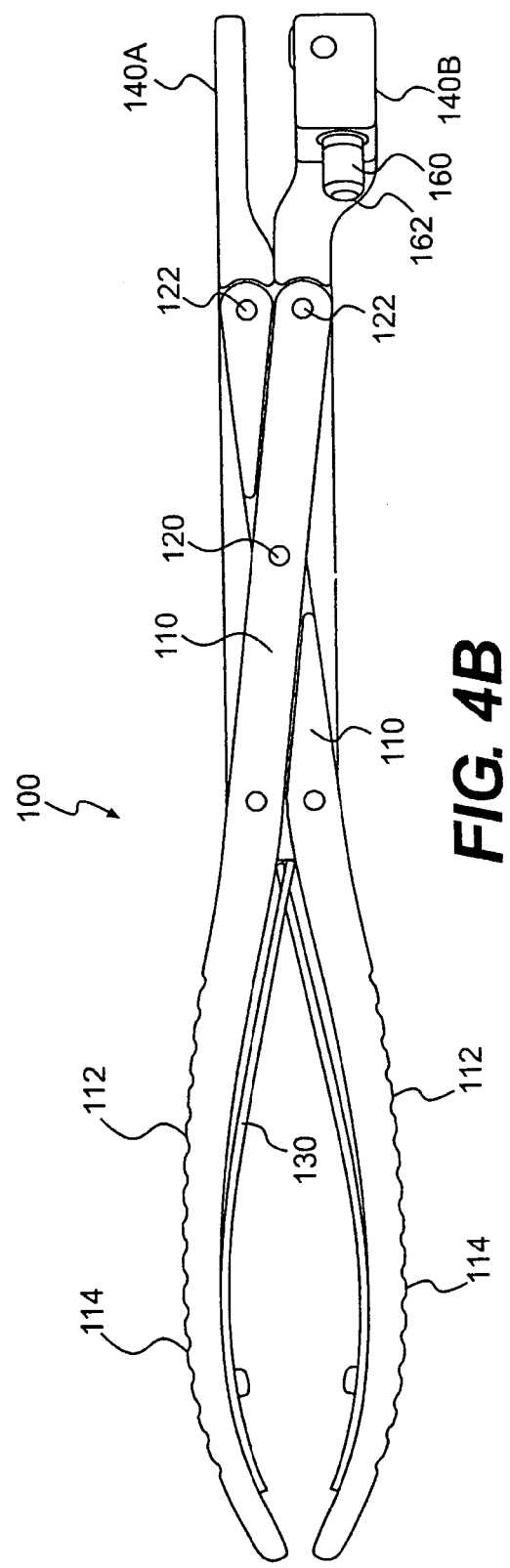
FIG. 4B illustrates a top view of the insertion tool of FIG. 4A.

FIGS. 4A and 4B illustrate an insertion tool 100 useful for assembling the bone fastener 60 during implantation. The insertion tool 100 may comprise a pair of handles 110 extending into gripping portions 112. The gripping portions 112 may include a surface modification such as raised portions 114 to provide a secure gripping surface for the user. The handles 110 are connected to one another with a pivotable hinge 120 in a manner similar to pliers and scissors, as is commonly known in the art. Extending distally from each handle 110 is an arm 115 that includes a bone fastener holding portion 140A, 140B. The arms 115 are connected to the handles 110 by a pivotable hinge connection 122. A leaf spring 130 may be positioned between the handles 110 to bias the holding portions 140A, 140B towards an open position.

Figure 7:
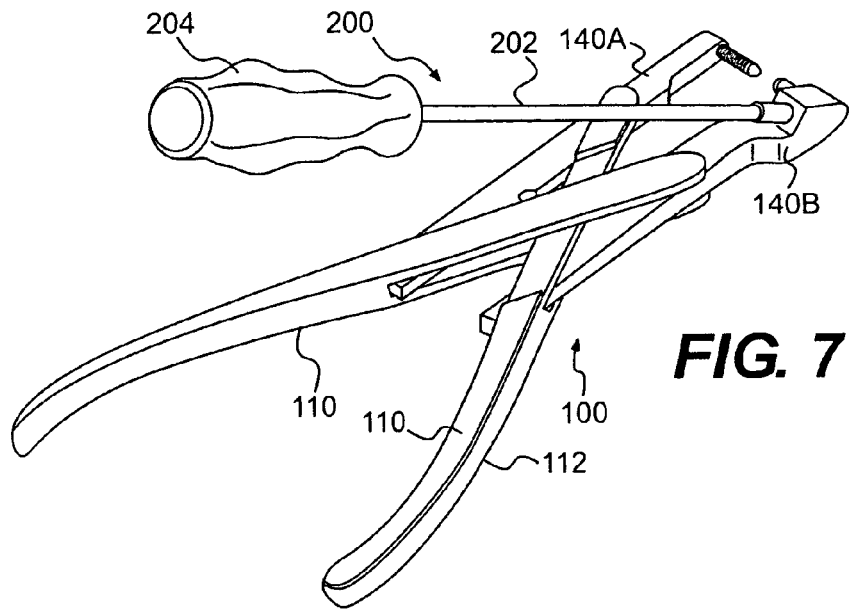
FIG. 7 illustrates a perspective view of the insertion tool of FIG. 5A and the bone fastener of FIG. 5B in use with the tightening instrument of FIG. 6A.
Figure 8:
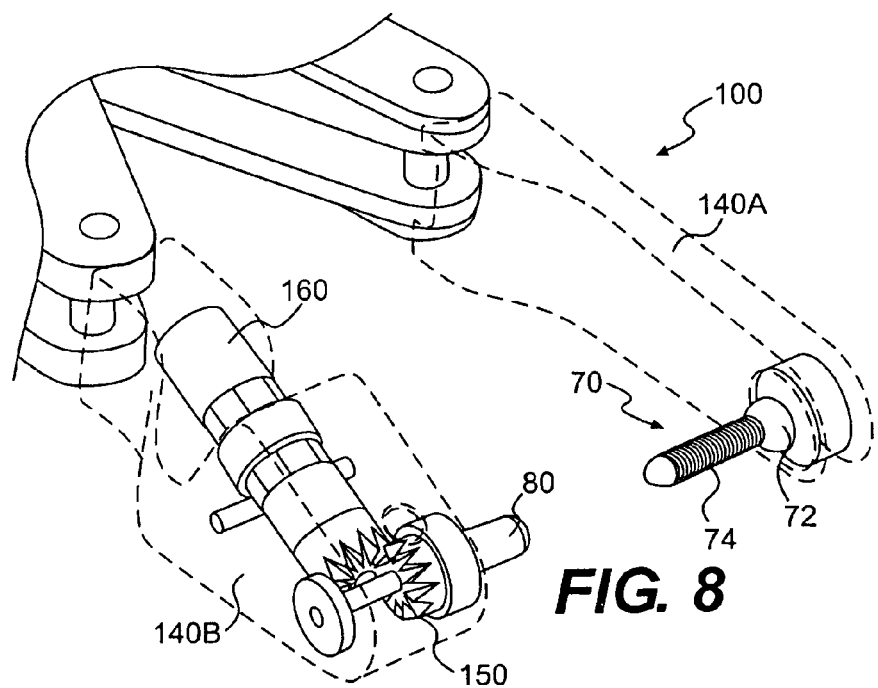
FIG. 8 illustrates a perspective view of the insertion tool of FIG. 5A and the bone fastener of FIG. 3.

As shown in greater detail in FIGS. 5B and 5C, the bone fastener holding portion 140A can include a cavity configured to securely hold the head 72 of the bolt 70 of bone fastener 60 during the implantation process, and the bone fastener holding portion 140B can include a second cavity configured to securely hold the head 82 of the nut 80, as shown in FIG. 8. Further, this bone fastener holding portion 140B may also include a gear mechanism 150, as shown in FIG. 5C. The gear mechanism 150 includes a port 160 extending from the bone fastener holding portion 140B. The port 160 can include a bore 162 configured to receive a tightening instrument 200, shown in FIGS. 6A and 6B. The tightening instrument 200 may comprise a shaft 202 extending proximally into a gripping portion 204 and distally into a tip 206 that is shaped and configured to fit complementarily within the bore 162 of port 160, as shown in FIG. 7.

Figure 9:
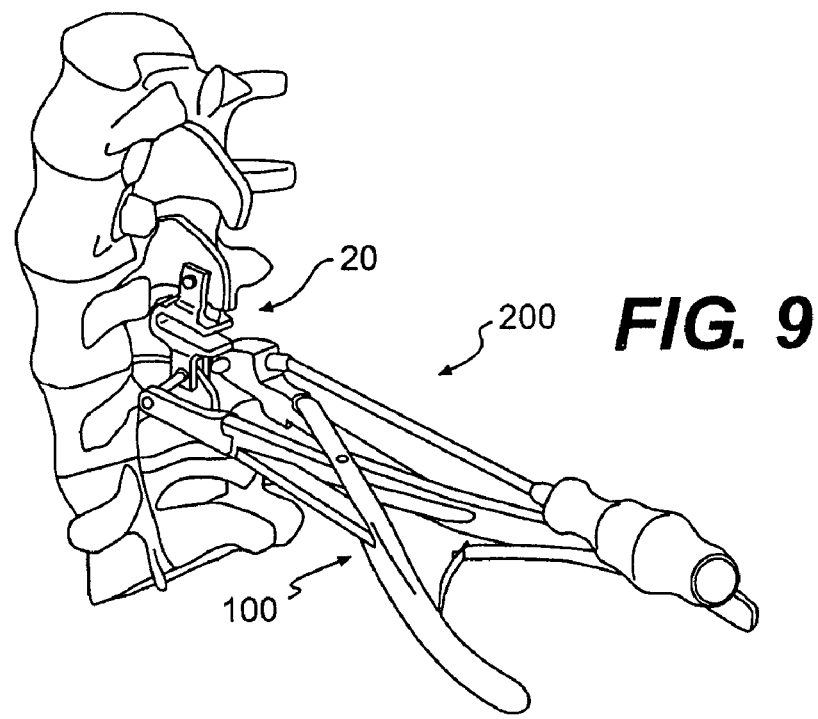
FIG. 9 is a perspective view of the implantation of the stabilization system using the insertion tool and tightening instrument of the present disclosure.
Figure 11A:
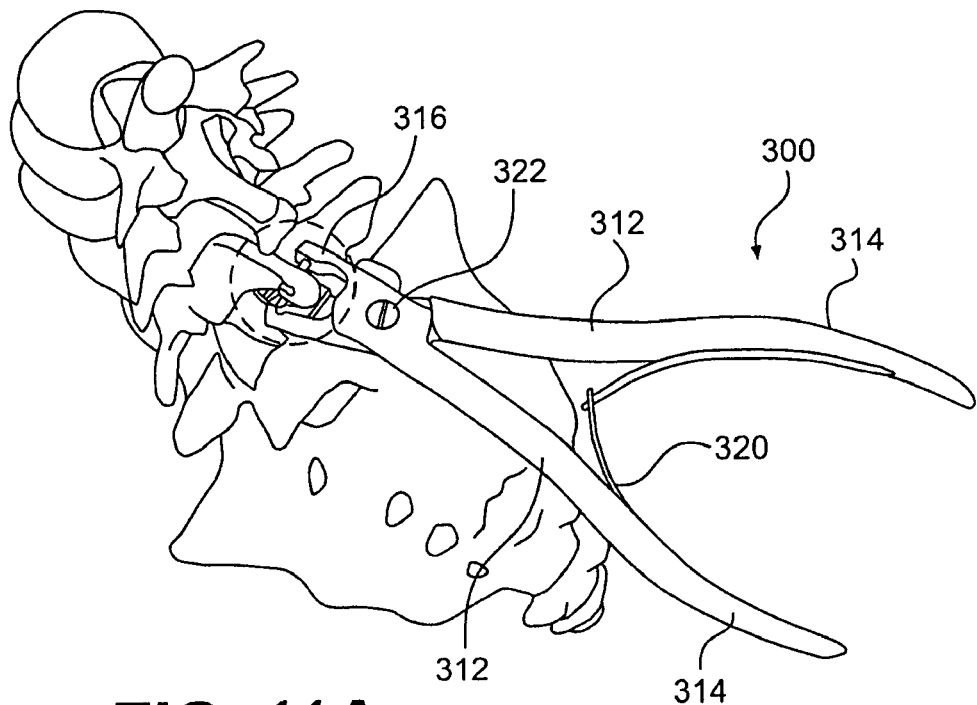
FIG. 11A illustrates a perspective view of a hole puncher tool that may be used during implantation of the interlaminar-interspinous vertebral stabilization system of the present disclosure.
Figure 11B:
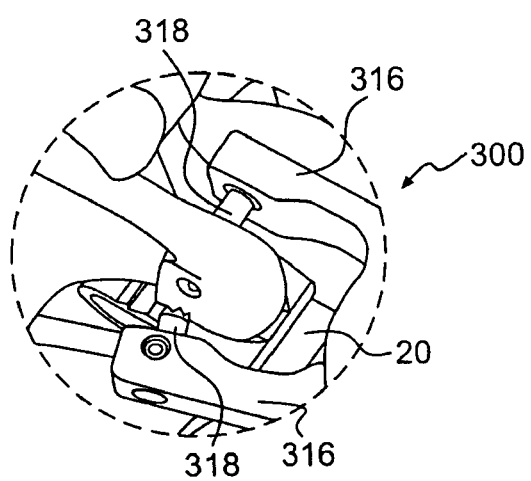
FIG. 11B illustrates an enlarged view of the hole puncher tool of FIG. 11A.

To assemble the system 10, the implantable device 20 is inserted between the spinous processes of adjacent vertebrae, as shown in FIG. 9. Any appropriate surgical approach may be used to expose/visualize the spinous processes. After the implantable device 20 has been properly aligned so that the spinous processes seat securely within the stirrups 38 of the device 20, a hole can be punched through the apertures 50 of each of the pair of lateral walls 36, the apertures serving as a guide for placement of the hole through the spinous processes and allowing the bone fastener 60 to be positioned in the hole and through the spinous process, as shown in FIGS. 11A and 11B. The holes may be formed using, for example, a hole puncher 300. The hole puncher 300 may comprise a pair of arms 312 connected by a leaf spring 320 and a pivotable hinge 322. The arms 312 extend proximally into gripping portions 314 and distally into claws 316. Extending from each claw 316 is a sharp cutting edge 318 suitable for cutting through bone.

As shown, the sharp cutting edge 318 may be shaped like a cylinder, matching the diameter of the aperture 50 of the implantable device. The sharp cutting edges 318 may be configured such that they receive and remove the bone as it is cut. For example, as shown, the cylindrical sharp cutting edges 318 can include a hollowed inner region that receives bone as it is cut. The cut bone is thereby held by the hole puncher 300 and can be removed after a hole is produced. To ensure that no extra bone material remains, a surgeon may elect to clean out the cut hole by inserting any suitable tool with a cylindrical tip having the same diameter as the hole, in one or more repeated steps as needed. Once the holes have been made and cleaned, the bone fasteners 60 may then be inserted through the apertures 50 of the lateral walls 36.

To secure the bone fasteners 60 to the seated device 20, the bolt 70 and nut 80 of a bone fastener 60 may be placed into the bone fastener holding portions 140A, 140B, respectively, of insertion tool 100. The insertion tool 100 is then positioned so as to align the bolt 70 and the nut 80 with the apertures 50 of the device 20. When it has been determined that the angle and location of the bolt 70 and nut 80 are correct, the tightening instrument 200 can be placed into the port 160. Turning the gripping portion 204 causes the rotation of the gear mechanism 150 and rotation of the nut 80, thereby causing the threading of the nut 80 onto the bolt 70.

The insertion tool facilitates alignment and threading of the bolt 70 and nut 80. For example, since there may be limited space available on lateral sides of the walls 36, it may be difficult for a surgeon to position the bolt 70 and nut 80 through a spinous process. The insertion tool 100 maintains the bolt 70 and nut 80 in the properly aligned position so as to ensure that they easily thread together during assembly. Further, the insertion tool 100, and accompanying tightening instrument 200, allow easy rotation of the nut 80 to secure the components to one another.

It will be understood that the tightening instrument 200 may be connected to the insertion tool 100 either before or after the bolt 70 and nut 80 are attached to the insertion tool 100, and a bone fastener 60 may be threaded through the superior section 34 of the spacer body 20 first, then an additional bone fastener 60 may be threaded through the inferior section 32, as shown in FIGS. 9 and 10. Additionally, the tightening instrument 200 enables the user to easily control the desired tightness by adjusting the number of clockwise and/or counter-clockwise turns of the gripping portion 204.

Figure 12:
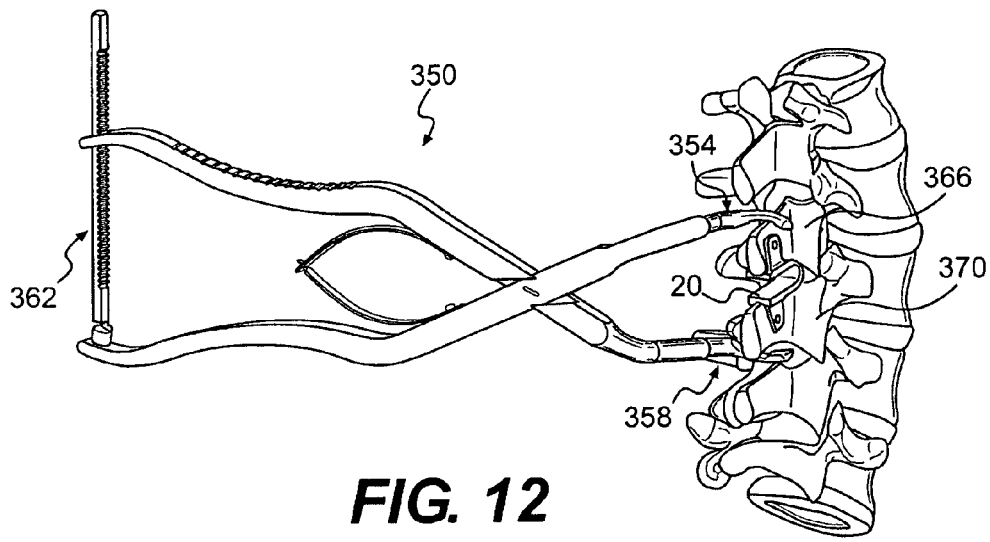
FIG. 12 illustrates a pair of compression pliers that may be used during implantation of the interlaminar-interspinous vertebral stabilization system of the present disclosure.
Figure 13:
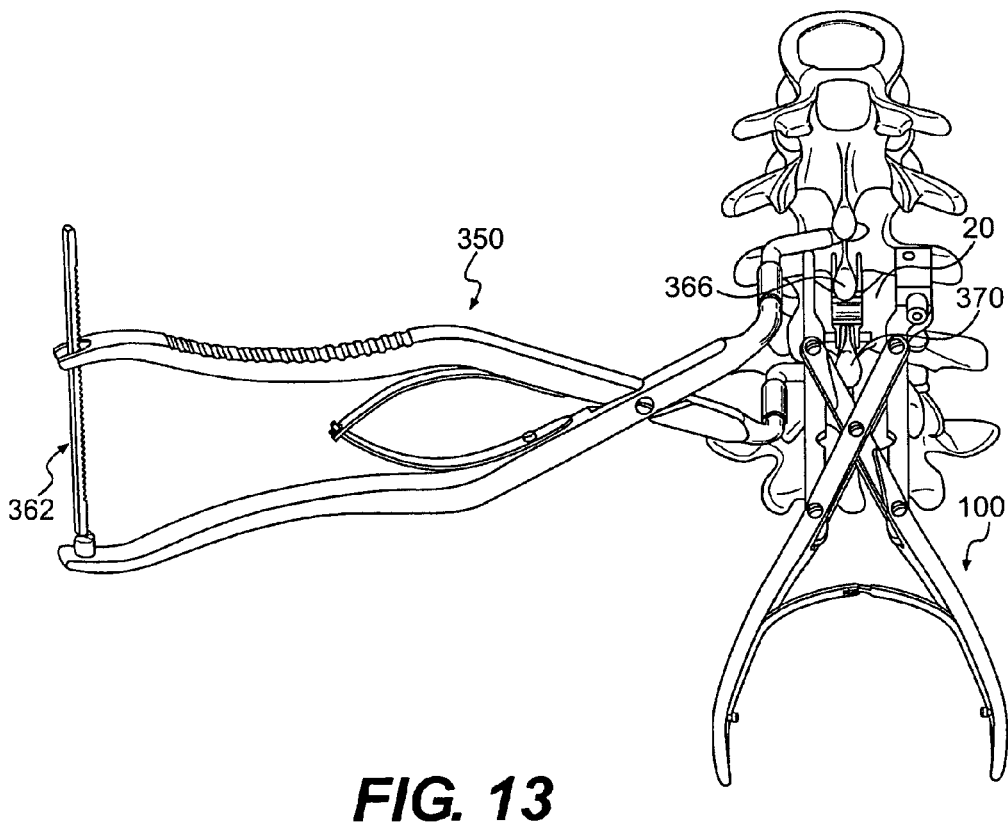
FIG. 13 illustrates the pair of compression pliers of FIG. 12 during implantation of the interlaminar-interspinous vertebral stabilization system of the present disclosure.

In some embodiments, one or more additional instruments may be provided to assist in positioning the spinous processes of the vertebrae to be treated. For example, to properly implant the device 20 between spinous processes of the lumbar vertebrae, it may be desirable to position the patient in a certain degree of lordosis. However, during surgery, the patient may not be positioned ideally. Therefore, to assist the surgeon in producing the desired degree of lordosis, a pair of compression pliers 350, as shown in FIG. 12, may be provided.

The compression pliers 350 can include two distal gripping portions 354, 358. The gripping portions 354, 358 can be pushed through the interspinous ligaments located superiorly and inferiorly to the spinous processes 366, 370 of a vertebral level to be treated. The gripping portions 354, 358 can then be compressed to push the spinous processes 366, 370 towards one another to fit within the stirrups 38 of an interlaminar-interspinous device 20.

Once properly positioned, the device 20 can be secured to the spinous processes 366, 370 using bone anchors 60 and the insertion tool 100 described previously. Further, to help maintain the spinous processes 366, 370 in the compressed position during insertion of bone anchors 60, the compression pliers 350 can include a locking mechanism 362. The locking mechanism can include, for example, a ratchet system positioned at the proximal portion of the compression pliers handles.

In some embodiments, the insertion tool 100, tightening instrument 200, hole puncher 300, and compression pliers 350 can be provided as an instrument set to be used with one or more devices 20. Accordingly, the insertion tool 100 and hole puncher can be sized and shaped such that a hole produced with the hole puncher 300 can be properly aligned with a bolt 70 and nut 80 provided held by the insertion tool 100.

By firmly securing the implantable device 20 to the spinous processes with the bone fasteners 60, fusion of bony tissue can be promoted. Further, if desired, additional bone-growth material, such as a bone graft, may be placed within the midsection 30 of the implantable device 20 to enhance bone growth and fusion. It is understood, of course, that other growth-promoting surface modifications such as, for example, pores or holes may be provided on the surfaces of the implantable device 20 to effect such ingrowth, as previously described.

In addition, although the device 20 is described with superior and inferior lateral walls 36, the device 20 can include a U-shaped implant with a single pair of lateral walls 36. Such devices may be used, for example, at the L5-S1 vertebral level. For example, the device 20 may include a single pair of lateral walls 36 configured to engage the spinous process of the L5 vertebra. Further, the device 20 may include a mechanism for securing the inferior section 32 to the sacrum. As noted above, the superior lateral walls can be secured to the L5 spinous process with a bone anchor 60, thereby limiting movement at the L5-S1 level and promoting fusion at that level. Various devices and mechanisms for securing the device 20 to the sacrum are described in co-pending U.S. patent application Ser. No. 11/400,586, which was filed on Apr. 7, 2006, and is herein incorporated by reference in its entirety.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An implantable interlaminar-interspinous stabilization system comprising:
   a U-shaped implantable device comprising an inferior section, a superior section, a midsection extending therebetween, and a pair of lateral walls extending from at least one of the inferior section and superior section for engaging a spinous process of a vertebra, each of the lateral walls including an aperture for receiving a bone fastener;
   a bone fastener for securing the implantable device to the spinous process;
   an insertion tool for inserting the bone fastener through the apertures of the implantable device during implantation of the system; and
   a tightening tool configured to cooperate with the insertion tool such that rotation of the tightening tool effects threading of the bolt and nut together.

2. The system of claim 1, wherein the bone fastener comprises a threaded bolt and a threaded nut.

3. The system of claim 1, wherein each aperture of the lateral walls includes a countersink.

4. The system of claim 1, wherein the pair of lateral walls extends from the superior section and the system further comprises:
   a second pair of lateral walls extending from the inferior section, each of the lateral walls of the second pair of lateral walls including an aperture for receiving a bone fastener.

5. The system of claim 4, further comprising a second bone fastener comprising a threaded bolt and a threaded nut.

6. The system of claim 4, further including a pair of compression pliers for positioning two spinous processes between the first and second pair of lateral walls, respectively.

7. The system of claim 1, further including a hole puncher configured to punch a hole through bony tissue of the spinous process to create a hole configured to receive the bone fastener.

8. The system of claim 7, wherein the hole puncher removes bony tissue excised from the spinous process to produce the hole.

9. The system of claim 1, wherein the midsection is compressible.

10. The system of claim 1, wherein the midsection is configured to act as a flexible hinge.

11. The system of claim 1, wherein the pair of lateral walls are movable relative to one another.

12. The system of claim 1, wherein the pair of lateral walls are movable relative to the inferior section or superior section from which the lateral walls extend.

13. A method of stabilizing a spine, comprising:
selecting a vertebral level to be treated;
positioning a U-shaped implant between two adjacent spinous processes of the selected vertebral level, the implant comprising:
an inferior section, a superior section, a midsection extending therebetween, and a first pair of lateral walls extending from at least one of the inferior section and superior section, each of the lateral walls including an aperture for receiving a bone fastener, wherein the pair of lateral walls are positioned on opposite sides of a spinous process of the selected vertebral level; and
creating a hole in the spinous process located between the two lateral walls of the implant before passing a bolt through the apertures of the lateral walls; and
securing the implant to at least one of the adjacent spinous processes by passing the bolt through the aperture of one of the lateral walls.

14. The method of claim 13, wherein securing the implant includes aligning a nut with the aperture of the lateral wall located on the opposite side of the spinous process as the bolt such that the passes through the spinous process and joins the nut at a threaded connection.

15. The method of claim 14, further including tightening the threaded connection between the nut and bolt to prevent movement of the implantable device relative to the vertebral level and promote fusion of the vertebral level.

16. The method of claim 14, further including using an alignment tool to pass the nut and bolt through the apertures of the lateral walls, the alignment tool configured to hold the nut and bolt and align threaded portions of the nut and bolt.

17. The method of claim 16, further including tightening the threaded connection between the nut and bolt by turning a gear mechanism of the alignment tool to rotate the nut relative to the bolt and thread the nut to the bolt.

18. The method of claim 14, wherein the pair of lateral walls extends from the superior section and is positioned on opposite sides of a first spinous process; and
the method further includes positioning a second pair of a second pair of lateral walls on opposite sides of a second spinous process, each of the lateral walls extending from the inferior section and including an aperture for receiving a bone fastener and are positioned.

19. The method of claim 18, wherein the method includes:
securing the implant to the first spinous process by passing a first bolt through the aperture of one of the lateral walls of the first pair of lateral walls; and
securing the implant to the second spinous process by passing a second bolt through the aperture of one of the lateral walls of the second pair of lateral walls.

20. The method of claim 19, wherein securing the implant comprises:
aligning a first nut with the aperture of the lateral wall located on the opposite side of the first spinous process as the first bolt such that the first bolt passes through the first spinous process and joins the first nut at a threaded connection; and
aligning a second nut with the aperture of the lateral wall located on the opposite side of the second spinous process as the second bolt such that the second bolt passes through the second spinous process and joins the second nut at a threaded connection.

21. The method of claim 19, further including tightening the threaded connections between the nuts and bolts to prevent movement of the implantable device relative to the vertebral level and promote fusion of the vertebral level.

22. The method of claim 21, further including using an alignment tool to pass the nuts and bolts through the apertures of the lateral walls, the alignment tool configured to hold the one of the nuts and one of the bolts and align threaded portions of the nut and bolt.

23. The method of claim 22, further including tightening the threaded connections between the nuts and bolts by turning a gear mechanism of the alignment tool to rotate the one of the nuts relative to one of the bolts and thread the nut to the bolt.

24. The method of claim 19, further including creating a hole in each of the first spinous process and second spinous process before passing the bolts and nuts through the apertures of the lateral walls.

25. The method of claim 24, wherein creating the hole includes passing a portion of a punching tool through at least one aperture of the lateral walls and through bony tissue of the spinous process.

26. The method of claim 19, further including moving the first spinous process and the second spinous process towards one another before securing the implant to the first spinous process and second spinous process.

27. The method of claim 26, wherein moving the first spinous process and the second spinous process towards one another includes engaging a top surface of one of the first and second spinous processes with a first portion of a pair of compression pliers, engaging a bottom surface of the other of the first and second spinous processes with a second portion of a compression pliers, and compressing the first and second portions of the compression pliers.

28. The method of claim 13, wherein creating the hole includes passing a portion of a punching tool through at least one aperture of the lateral walls and through bony tissue of the spinous process.

29. An implantable interlaminar-interspinous stabilization system comprising:
a U-shaped implantable device comprising an inferior section, a superior section, a midsection extending therebetween, and a pair of lateral walls extending from each of the inferior section and superior section for engaging a spinous process of a vertebra, each of the lateral walls including an aperture for receiving a bone fastener, each of the lateral walls including an aperture for receiving a bone fastener, wherein each aperture of the lateral walls includes a countersink;
a bone fastener for securing the implantable device to the spinous process;
an insertion tool for inserting the bone fastener through the apertures of the implantable device during implantation of the system; and
a pair of compression pliers for positioning a spinous process between each pair of lateral walls.

30. A method of stabilizing a spine, comprising:
selecting a vertebral level to be treated;

positioning a U-shaped implant between two adjacent spinous processes of the selected vertebral level, the implant comprising:

an inferior section, a superior section, a midsection extending therebetween, and a first pair of lateral walls extending from at least one of the inferior section and superior section, each of the lateral walls including an aperture for receiving a bone fastener, wherein the pair of lateral walls are positioned on opposite sides of a spinous process of the selected vertebral level; and securing the implant to at least one of the adjacent spinous processes by using an alignment tool to pass a nut and bolt through the apertures of the lateral walls, wherein the step of securing includes aligning the nut with the aperture of the lateral wall located on the opposite side of the spinous process as the bolt such that the bolt passes through the spinous process and joins the nut at a threaded connection, and wherein the alignment tool is configured to hold the nut and bolt and align threaded portions of the nut and bolt.

31. The method of claim 30, further including tightening the threaded connection between the nut and bolt by turning a gear mechanism of the alignment tool to rotate the nut relative to the bolt and thread the nut to the bolt.

32. A method of stabilizing a spine, comprising:

selecting a vertebral level to be treated;

positioning a U-shaped implant between two adjacent spinous processes of the selected vertebral level, the implant comprising:

an inferior section, a superior section, a midsection extending therebetween, and a first pair of lateral walls extending from at least one of the inferior section and superior section, each of the lateral walls including an aperture for receiving a bone fastener, wherein the pair of lateral walls are positioned on opposite sides of a spinous process of the selected vertebral level;

moving a first spinous process and a second spinous process towards one another before securing the implant to the first spinous process and second spinous process by engaging a top surface of one of the first and second spinous processes with a first portion of a pair of compression pliers, engaging a bottom surface of the other of the first and second spinous processes with a second portion of a compression pliers, and compressing the first and second portions of the compression pliers; and securing the implant to a first spinous process by passing a first bolt through the aperture of one of the lateral walls of the first pair of lateral walls, securing the implant to a second spinous process by passing a second bolt through the aperture of one of the lateral walls of the second pair of lateral walls, wherein securing the implant includes aligning a nut with the aperture of the lateral wall located on the opposite side of the spinous process as the bolt such that the bolt passes through the spinous process and joins the nut at a threaded connection.

\* \* \* \* \*